(12) United States Patent
Pintoffl et al.

(10) Patent No.: US 11,045,170 B2
(45) Date of Patent: Jun. 29, 2021

(54) METHOD AND SYSTEM FOR ACQUISITION, ENHANCED VISUALIZATION, AND SELECTION OF A REPRESENTATIVE PLANE OF A THIN SLICE ULTRASOUND IMAGE VOLUME

(71) Applicant: General Electric Company, Schenectady, NY (US)

(72) Inventors: Klaus Pintoffl, Oberösterreich (AT); Christian Fritz Perrey, Oberösterreich (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1645 days.

(21) Appl. No.: 14/925,238

(22) Filed: Oct. 28, 2015

(65) Prior Publication Data

US 2017/0119355 A1    May 4, 2017

(51) Int. Cl.
*A61B 8/08*     (2006.01)
*A61B 8/00*     (2006.01)
(Continued)

(52) U.S. Cl.
CPC .............. *A61B 8/523* (2013.01); *A61B 8/145* (2013.01); *A61B 8/4444* (2013.01);
(Continued)

(58) Field of Classification Search
CPC ............. G01S 7/52063; G01S 15/8993; G01S 7/52098
See application file for complete search history.

(56) References Cited

U.S. PATENT DOCUMENTS 5,873,830 A * 2/1999 Hossack ............. G01S 7/52046 600/447
2003/0007598 A1* 1/2003 Wang ................... A61B 8/5238 378/37

(Continued)

FOREIGN PATENT DOCUMENTS

WO    WO2014179277 A1 * 11/2014    ............... A61B 8/13
WO    WO2014191479 A1 * 12/2014    ............... A61B 8/14

OTHER PUBLICATIONS

Price and Links in "Medical Imaging Signals and Systems" Price and Links edts, Pearson and Prentica Hall 2005—Chapter 11.*

(Continued)

*Primary Examiner* — Keith M Raymond
*Assistant Examiner* — Patrick M Mehl
(74) *Attorney, Agent, or Firm* — McAndrews, Held & Malloy, Ltd.; Jacob Groethe; David Bates (57) ABSTRACT

An ultrasound device performs a two-dimensional (2D) ultrasound scan to acquire a plurality of 2D images based on 2D ultrasound scan parameters. The ultrasound system stops the 2D ultrasound scan in response to an instruction received by a processor of the ultrasound system. The ultrasound device performs a thin slice volume ultrasound scan in response to the instruction to acquire a thin slice volume. The thin slice volume includes a last acquired 2D image of the 2D ultrasound scan and one or more 2D images adjacent to the last acquired 2D image. The ultrasound system identifies at least one representative plane from the thin slice volume. The ultrasound system displays the identified at least one representative plane at a display system.

20 Claims, 2 Drawing Sheets

(51) Int. Cl.
*A61B 8/14* (2006.01)
*G01S 7/52* (2006.01)
*G01S 15/89* (2006.01)

(52) U.S. Cl.
CPC ............ *A61B 8/4494* (2013.01); *A61B 8/466* (2013.01); *A61B 8/467* (2013.01); *A61B 8/54* (2013.01); *G01S 7/52063* (2013.01); *G01S 7/52098* (2013.01); *G01S 15/8993* (2013.01)

(56) References Cited

U.S. PATENT DOCUMENTS

| | | | | |
|---|---|---|---|---|
| 2005/0228280 | A1* | 10/2005 | Ustuner | A61B 8/06 600/443 |
| 2006/0084871 | A1* | 4/2006 | Akaki | A61B 8/13 600/437 |
| 2010/0260398 | A1* | 10/2010 | Ma | A61B 6/469 382/131 |
| 2013/0281854 | A1* | 10/2013 | Stuebe | A61B 8/13 600/440 |
| 2013/0345563 | A1* | 12/2013 | Stuebe | A61B 5/04012 600/440 |
| 2015/0196280 | A1* | 7/2015 | Yamamoto | A61B 8/4461 600/440 |
| 2015/0250455 | A1* | 9/2015 | Lee | G06T 7/73 382/131 |
| 2015/0257738 | A1* | 9/2015 | Kim | A61B 8/468 600/440 |

OTHER PUBLICATIONS

Pooh et al. 2012 The Journal of Maternal-Fetal and Neonatal Medicine 25: 433-455.*
Lacefield presentation Diagnostic Radiology Physics: A Handbook for Teachers and Students; Chap.13 Ultrasound Imaging, Pub.Date 2014 (Year: 2014).*
Fenster et al. 2001 Proc. SPIE 4549 Medical Image Acquisition and Processing 10 pages (Year: 2001).*

* cited by examiner

METHOD AND SYSTEM FOR ACQUISITION, ENHANCED VISUALIZATION, AND SELECTION OF A REPRESENTATIVE PLANE OF A THIN SLICE ULTRASOUND IMAGE VOLUME

CROSS-REFERENCE TO RELATED APPLICATIONS/INCORPORATION BY REFERENCE

[Not Applicable]

FIELD OF THE INVENTION

Certain embodiments of the invention relate to ultrasound imaging. More specifically, certain embodiments of the invention relate to a method and system for acquisition, enhanced visualization, and selection of at least one representative plane of a thin slice ultrasound image volume.

BACKGROUND OF THE INVENTION

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images. In various applications, measurements may be performed on the acquired ultrasound image data to provide information regarding a health condition. For example, in obstetric ultrasound, various measurements can provide information on the size, weight, gestational age, and potential health conditions of the fetus. As an example, fetal head measurements may be used to assess the size and growth of the fetus. As another example, nuchal translucency and nuchal fold measurements may be performed to help identify an increased likelihood of congenital heart defect or chromosomal conditions, such as Down syndrome and Turner syndrome.

Typically, two-dimensional (2D) ultrasound images may be acquired and the image structures may be measured to detect various conditions. However, 2D acquisition in medical ultrasound has the disadvantage that if the imaging plane is not correct when the image is frozen, the ultrasound operator is unable to adjust the plane. For example, in a mid-sagittal view of a fetus, the nasal tip could be missing making the image unusable for nuchal translucency measurements and requiring the ultrasound operator to acquire additional ultrasound image data. As another example, if a measurement is to be performed on a largest width or diameter of a structure and the width or diameter shown in the selected plane is not at its largest, the measurement may provide a false negative or false positive of an associated condition.

A selected plane from three-dimensional (3D) or four-dimensional (4D) ultrasound images may also be used to perform measurements. However, 3D and 4D ultrasound is more complicated and time-consuming to set-up. Moreover, the frame rate is usually much lower than in 2D ultrasound, resulting in the physical resolution of an image plane being much lower. 3D or 4D ultrasound also records substantially more ultrasound data and much of this data is unused to perform the needed measurements. Furthermore, the manipulations of the 3D or 4D ultrasound data needed to identify one desired plane can be cumbersome.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

A system and/or method is provided for acquisition, enhanced visualization, and selection of at least one representative plane of a thin slice ultrasound image volume, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

Certain embodiments of the invention may be found in a method and system for acquisition, enhanced visualization, and selection of at least one representative plane of a thin slice ultrasound image volume. For example, aspects of the present invention have the technical effect of providing a two-dimensional (2D) image acquisition workflow to acquire a thin slice ultrasound volume. Moreover, aspects of the present invention have the technical effect of instantaneously transitioning between 2D image acquisition and the acquisition of a thin slice ultrasound volume based on a user input, such as the depression of a freeze button. Additionally, aspects of the present invention have the technical effect of dynamically determining a volume thickness based on an amount of time a user input is provided, such as the length of time the freeze button is depressed. Furthermore, aspects of the present invention have the technical effect of automatically or semi-automatically selecting at least one 2D ultrasound image from a thin slice volume based at least in part on a desired measurement, an examination type, or the like.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the invention, such as single or multi-core: CPU, Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

Figure 1:
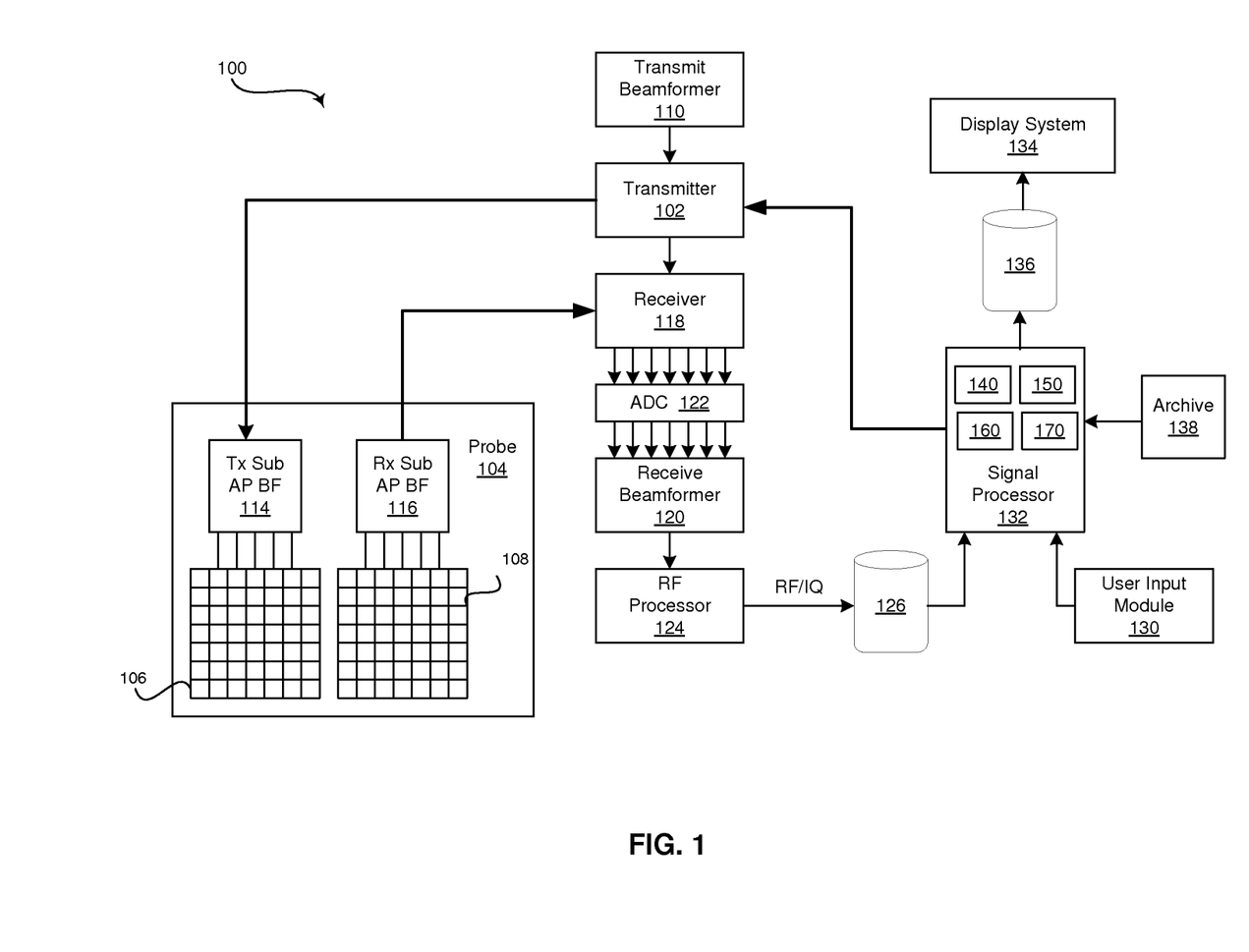
FIG. 1 is a block diagram of an exemplary ultrasound system that is operable to provide acquisition, enhanced visualization, and selection of at least one representative plane of a thin slice ultrasound image volume, in accordance with an embodiment of the invention.

FIG. 1 is a block diagram of an exemplary ultrasound system 100 that is operable to provide acquisition, enhanced visualization, and selection of at least one representative plane of a thin slice ultrasound image volume, in accordance with an embodiment of the invention. Referring to FIG. 1, there is shown an ultrasound system 100 comprising a transmitter 102, an ultrasound probe 104, a transmit beamformer 110, a receiver 118, a receive beamformer 120, a RF processor 124, a RF/IQ buffer 126, a user input module 130, a signal processor 132, an archive 138, an image buffer 136, and a display system 134.

The transmitter 102 may comprise suitable logic, circuitry, interfaces and/or code that may be operable to drive an ultrasound probe 104. The ultrasound probe 104 may comprise a one dimensional (1D, 1.25D, 1.5D or 1.75D) array, two dimensional (2D) array, or three dimensional (3D) array of piezoelectric elements. The ultrasound probe 104 may comprise a group of transmit transducer elements 106 and a group of receive transducer elements 108, that normally constitute the same elements.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals 107 may be back-scattered from structures in the object of interest, like blood cells or tissue, to produce echoes. The echoes are received by the receive transducer elements 108. The group of receive transducer elements 108 in the ultrasound probe 104 may be operable to convert the received echoes into analog signals, undergo sub-aperture beamforming by a receive sub-aperture beamformer 116 and are then communicated to a receiver 118.

The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122. The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the invention is not limited in this regard. Accordingly, in some embodiments of the invention, the plurality of A/D converters 122 may be integrated within the receiver 118.

The receive beamformer 120 may comprise suitable logic, circuitry, interfaces and/or code that may be operable to perform digital beamforming processing on the signals received from the plurality of A/D converters 122. The resulting processed information may be converted back to corresponding RF signals. The corresponding output RF signals that are output from the receive beamformer 120 may be communicated to the RF processor 124. In accordance with some embodiments of the invention, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment of the invention, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input patient data, image acquisition and scan parameters, settings, configuration parameters, change scan mode, and the like. In an exemplary embodiment of the invention, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, and/or the display system 134.

In various embodiments, the user input module 130 may be operable to provide 2D ultrasound scan parameters. For example, a user may input 2D image acquisition parameters, such as image depth, image width, focus position, number of foci, line density, gain, and transmission pulse patter, among other things, using the user input module 130. Additionally and/or alternatively, a user may select a preset that defines a set of 2D image acquisition parameters using the user input module 130. As another example, the user may select an ultrasound probe type, an examination type, and/or a measurement type. For example, the user may select a nuchal translucency examination type and measurement.

In an exemplary embodiment, the user input module 130 may be operable to receive instructions for controlling the ultrasound scan. For example, as a 2D ultrasound scan is being performed, the user input module 130 may provide an instruction to stop the 2D ultrasound scan and instantaneously begin a thin slice volume ultrasound scan. The user input module 130 can be a freeze button or any suitable button, switch, touch screen input, mousing device input, keyboard input, remote control input, voice command, or the like. As an example, depressing a freeze button may stop the 2D ultrasound scan and continuing to hold the freeze button may begin a thin slice volume ultrasound scan where the thin slice volume includes the last 2D frame from the 2D ultrasound scan and one or more 2D images adjacent to the last acquired 2D image of the 2D ultrasound scan. In various embodiments, the adjacent 2D images are in parallel to the last acquired 2D image of the 2D ultrasound scan. In an exemplary embodiment, the thin slice volume may be generated by a volumetric sweep, where the adjacent 2D images are acquired in a fan-like approach. In various embodiments, the thickness of the thin slice volume ultrasound scan may be dependent on a length of time the freeze button is held, a predetermined thickness, or a default thickness, among other things. For example, the user may input that the predetermined thickness is 2 millimeters. In certain embodiments, a thickness of the thin slice volume acquired using the 2D image acquisition workflow described in the present application may be 1 millimeter to 10 millimeters.

In an exemplary embodiment, the user input module 130 may be operable to receive a selection identifying one more ultrasound images to store in an archive 138. For example, a user may activate a button 130 on the ultrasound probe 104 to accept and store one or more frames from the 2D ultrasound scan and/or the thin slice volume scan. The accepted and stored ultrasound images may include, for example, a 2D image in a plane of the thin slice volume ultrasound scan that is identified automatically and/or semi-automatically by the plane selection module 150 of the signal processor 132 as described below. The user input module 130 can include a mousing device, keyboard, touch screen display, remote control, button, switch, sliding bar, voice activated input, and/or any suitable device or mechanism operable to receive a user input. The user input module 130 may be integrated with other components, such as the ultrasound probe 104 or display system 134, or can be a separate component.

The signal processor 132 may comprise suitable logic, circuitry, interfaces and/or code that may be operable to process the ultrasound scan data for generating an ultrasound image for presentation on a display system 134. The signal processor 132 is operable to perform one or more processing operations according to a plurality of selectable ultrasound modalities on the acquired ultrasound scan data. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In the exemplary embodiment, the signal processor 132 may comprise a thin slice volume module 140, a plane selection module 150, a measurement module 160, and an examination analysis module 170.

The ultrasound system 100 may be operable to continuously acquire ultrasound information at a frame rate that is suitable for the imaging situation in question. Typical frame rates range from 20-70 but may be lower or higher. The acquired ultrasound information may be displayed on the display system 134 at a display-rate that can be the same as the frame rate, or slower or faster. An image buffer 136 is included for storing processed frames of acquired ultrasound information that are not scheduled to be displayed immediately. Preferably, the image buffer 136 is of sufficient capacity to store at least several seconds worth of frames of ultrasound information. The frames of ultrasound information are stored in a manner to facilitate retrieval thereof according to its order or time of acquisition. The image buffer 136 may be embodied as any known data storage medium.

The thin slice volume module 140 may comprise suitable logic, circuitry, interfaces and/or code that may be operable to control the transmitter 102 and/or transmit beamformer 110 for acquiring thin slice volume ultrasound image data of the target by controlling the emission of the ultrasonic transmit signals into a region of interest. The thin slice volume module 140 may control the transmitter 102 and/or transmit beamformer 110 for acquiring the thin slice volume ultrasound image data in response to an instruction received from a user input module 130, a selected preset, a default mode, or the like. For example, during a 2D ultrasound scan, an ultrasound operator may depress and hold a freeze button, or any suitable user input device 130, to stop the 2D ultrasound scan and begin a thin slice volume ultrasound scan. Specifically, the thin slice volume module 140, in response to receiving the press and hold freeze button signal, controls the transmitter 102 and/or transmit beamformer 110 to acquire 2D image slices adjacent to the last acquired frame of the 2D ultrasound scan. The last acquired image of the 2D ultrasound scan along with the adjacent 2D images form the thin slice volume. In various embodiments, the adjacent 2D images are in parallel to the last acquired 2D image of the 2D ultrasound scan. In an exemplary embodiment, the thin slice volume may be generated by a volumetric sweep, where the adjacent 2D images are acquired in a fan-like approach.

As an example, after depressing and holding a freeze button for approximately 100 milliseconds or any suitable duration, the thin slice volume ultrasound scan may begin. If the ultrasound operator holds the freeze button for over 250 milliseconds or any suitable duration, the thin slice volume module 140 may store the thin slice volume in memory, such as the image buffer 136 or the archive 138, which may be a local archive or PACS, for example. The thin slice volume may be acquired using the 2D ultrasound image acquisition parameters used for the 2D ultrasound scan. The thin slice volume may be a volume having a thickness of 1 millimeter to 10 millimeters. The thickness of the thin slice volume may be a default value, a predetermined value set by an operator using the user input module 130, or a dynamically determined value based on an instruction from the user input module 130 during the thin slice volume ultrasound scan. For example, the thickness of the thin slice volume can be dynamically determined based on the length of time the freeze button is held down, where the longer the button is held, the more adjacent 2D images are acquired and the thicker the thin slice volume. The thin slice volume module 140 may be operable to control the transmitter 102 and/or transmit beamformer 110 to acquire the thin slice volume based at least in part on the default, predetermined, or dynamically determined thickness, for example. The thin slice volume module 140 may be operable to acquire the thin slice volume in accordance with a 2D ultrasound scan workflow, such that the thin slice volume slices are acquired nearly immediately after the 2D ultrasound scan using the same 2D ultrasound scan image acquisition parameters and having substantially the same image quality as the 2D ultrasound scan images.

The plane selection module 150 may comprise suitable logic, circuitry, interfaces and/or code that may be operable to automatically and/or semi-automatically identify a representative 2D ultrasound image from the plurality of adjacent 2D images in the thin slice volume. The automatic and/or semi-automatic selection may be based, at last in part, on a selected measurement type, an examination type, or the like. For example, if a user selects a nuchal translucency examination type and/or measurement, the plane selection module 150 can select the mid sagittal image having the tip of the nose, nasal bone, hard palate, and diencephalon. As another example, if a user is measuring a vessel diameter, the plane selection module may select the 2D image from the thin slice volume that includes the length of the vessel and showing the largest diameter. In certain embodiments, the plane selection module 150 may define and generate a 2D image slice that is angled across two or more adjacent slices.

The plane selection module 150 of the signal processor 132 may apply image detection techniques and/or algorithms to automatically and/or semi-automatically select at least one representative 2D ultrasound image from the thin slice volume. In various embodiments, the plane selection module 150 may attempt to identify at least one representative 2D image automatically. The plane selection module 150 may display the automatically identified representative 2D image(s) at the display system 134. If a representative 2D image cannot be automatically identified or if the automatically identified image is not satisfactory to a user, the user may select and/or be prompted to select a region or structure in a displayed 2D image to assist the plane selection module 150 in performing a semi-automatic search of the thin slice volume 2D images based on the region and/or structured selected using the user input module 130. Additionally and/or alternatively, the plane selection module 150 may prompt a user for assistance at the onset prior to identifying at least one representative plane in the thin slice volume.

As used herein, the term "semi-automatically" refers to the exemplary embodiments where a user provides assistance to the plane selection module 150 by identifying a region or structure in the image data for the plane selection module 150 to apply its image detection techniques and/or algorithms. As used herein, the term "automatically" in the context of the plane selection module 150 refers to the exemplary embodiments where the plane selection module 150 selects at least one representative plane in the thin slice volume without user assistance.

Still referring to FIG. 1, the measurement module 160 may comprise suitable logic, circuitry, interfaces and/or code that may be operable to perform a selected measurement on the representative 2D plane identified by the plane selection module 150 and/or on one or more 2D planes selected by a user using, for example, the user input device 130. For example, the user may select one of the plurality of adjacent 2D images of the thin slice volume or may identify a plane across multiple 2D images in the thin slice volume by setting staple points on the image using the examination analysis module 170 as described below. The measurement module 160 may apply a nuchal translucency measurement, a nuchal fold measurement, a long bone measurement, a fetal head measurement, a vessel measurement, or any suitable measurement. In various embodiments, the measurement may be associated with an examination type or may be separately selected, among other things. The measurement module 160 may display the results of the measurement at the display system 134. The results of the measurement may be overlaid on the measured image or separately, among other things. The measurement may be stored with the measured image in the archive 138, which may be a local archive or PACS, for example.

The examination analysis module 170 may comprise suitable logic, circuitry, interfaces and/or code that may be operable to provide tools for post-processing and otherwise manipulating and storing 2D images and/or thin slice volumes that are displayed at the display system 134. For example, the examination analysis module 170 may be operable to perform 3D rendering, among other things, on the thin slice volumes. As another example, the examination analysis module 170 may be operable to manipulate the thin slice volumes to select a plane based on a user input received at the user input module 130. Specifically, after acquiring a thin slice volume or reloading a thin slice volume from an archive 138, a user can manually identify an image plane using various selection procedures.

In one exemplary embodiment, for example, a user may shift through the adjacent planes of the thin slice volume to set 3 markers or staple points in the thin slice volume. The user may also use Z-rotation to navigate the thin slice volume. After selecting the 3 staple points, a 2D image of the plane through all 3 markers is displayed at the display system 134. In another exemplary embodiment, for example, X, Y, and Z rotation may be used by a user to navigate the thin slice volume. After setting a first staple point, the first staple point may become a pivot point for rotating around to set a second staple point. The user then rotates around the line connecting the first and second staple points to select a third staple point. A 2D image of the plane passing through the first, second, and third staple points is displayed at the display system 134. In various embodiments, the staple points may remain visible in the thin slice volume, similar to a 3D region of interest.

Figure 2:
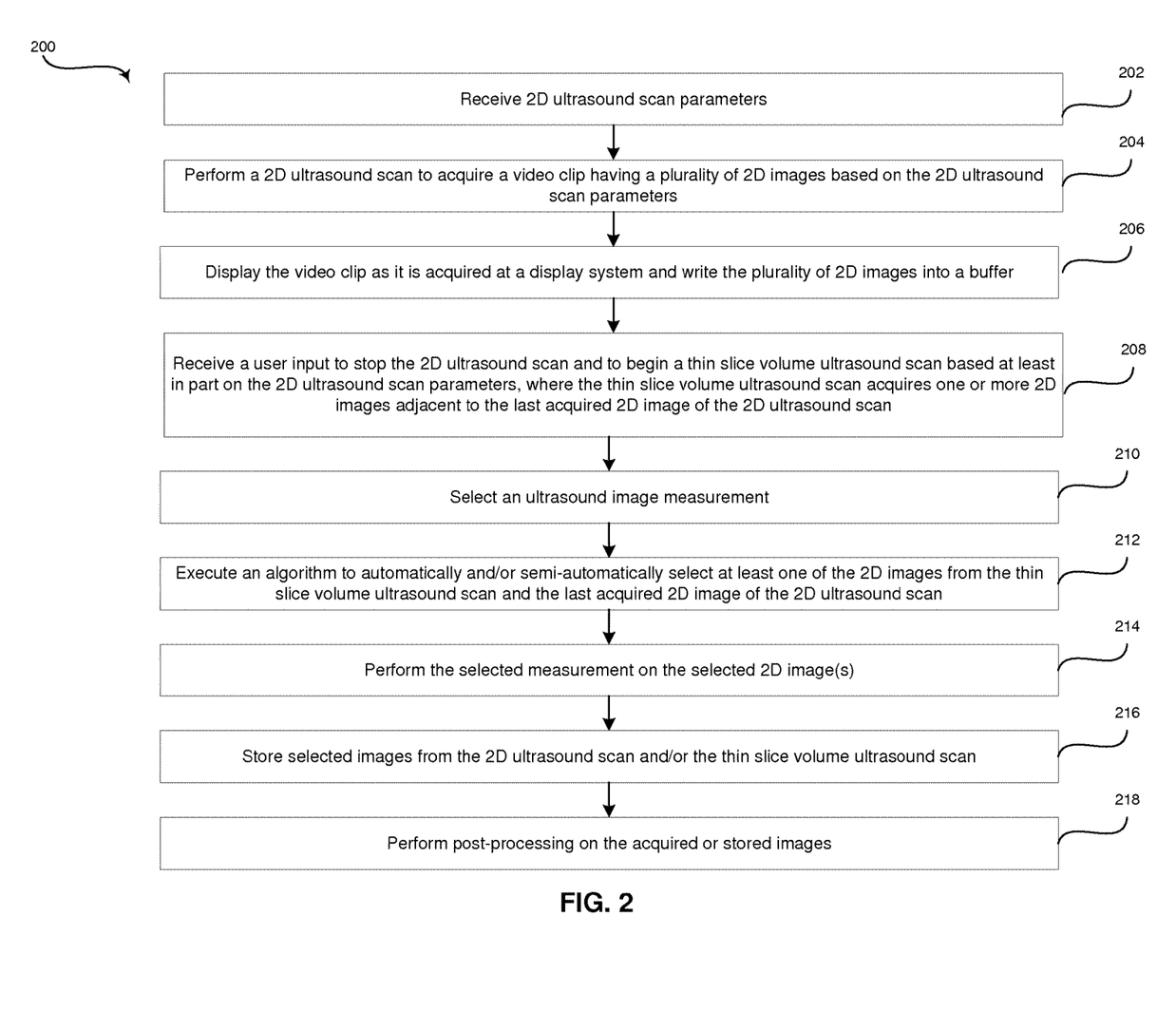
FIG. 2 is a flow chart illustrating exemplary steps that may be utilized for providing acquisition, enhanced visualization, and selection of at least one representative plane of a thin slice ultrasound image volume, in accordance with an embodiment of the invention.

FIG. 2 is a flow chart 200 illustrating exemplary steps 202-218 that may be utilized for providing acquisition, enhanced visualization, and selection of at least one representative plane of a thin slice ultrasound image volume, in accordance with an embodiment of the invention. Referring to FIG. 2, there is shown a flow chart 200 comprising exemplary steps 202 through 218. Certain embodiments of the present invention may omit one or more of the steps, and/or perform the steps in a different order than the order listed, and/or combine certain of the steps discussed below. For example, some steps may not be performed in certain embodiments of the present invention. As a further example, certain steps may be performed in a different temporal order, including simultaneously, than listed below.

At step 202, the ultrasound system 100 may receive scan parameters for a 2D ultrasound scan. For example, the signal processor 132 may receive 2D ultrasound scan parameters provided by the user input module 130. The scan parameters may include 2D image acquisition parameters, such as image depth, image width, focus position, number of foci, line density, gain, and transmission pulse patter, among other things. Additionally and/or alternatively, a preset may be selected by the user input module 130 that defines a set of 2D image acquisition parameters. The scan parameters provided by the user input module 130 can include an ultrasound probe type, an examination type, and/or a measurement type, among other things. For example, the user may select a nuchal fold examination type and measurement.

At step 204, the ultrasound probe 104 in the ultrasound system 100 may be operable to perform a 2D ultrasound scan. For example, the ultrasound probe 104 may acquire a video clip having a plurality of 2D images based on the 2D ultrasound parameters received at step 202.

At step 206, the video clip may be displayed at the display system 134 and written into a buffer. For example, as the plurality of 2D ultrasound images are acquired at step 204, the images may be written to an image buffer 136 and/or an archive 138 and may be continuously displayed at a display system 134.

At step 208, the signal processor 132 may receive a user input via the user input module 130 to stop the 2D ultrasound scan and to begin a thin slice volume ultrasound scan. For example, an ultrasound operator may depress and hold a freeze button, or any suitable user input device 130, to stop the 2D ultrasound scan and begin a thin slice volume ultrasound scan. The thin slice volume module 140, in response to receiving the press and hold freeze button signal, for example, controls the transmitter 102 and/or transmit beamformer 110 to acquire 2D image slices adjacent to the last acquired frame of the 2D ultrasound scan. The adjacent 2D images may be in parallel to the last acquired 2D image of the 2D ultrasound scan. Additionally and/or alternatively, the thin slice volume may be generated by a volumetric sweep, where the adjacent 2D images are acquired in a fan-like approach. The thin slice volume module 140 may be operable to instruct the transmitter 102 and/or transmit beamformer 110 to acquire the thin slice volume after the freeze button is pressed and held for approximately 100 milliseconds or any suitable duration. The thin slice volume module 140 may store the thin slice volume in an image buffer 136 or archive 138 when the freeze button is held for over 250 milliseconds or any suitable duration. The thin slice volume having a thickness of 1 millimeter to 10 millimeters may be acquired using the 2D ultrasound image acquisition parameters used for the 2D ultrasound scan. The specific thickness of the thin slice volume may be dynamically determined value based the length of time the freeze button is held down during the thin volume ultrasound scan, or can be a default value or a predetermined value set by an operator using the user input module 130. As an example, the longer the freeze button is held, the more adjacent 2D images may be acquired and the thicker the thin slice volume. In an exemplary embodiment, the thin slice volume slices are acquired directly after the 2D ultrasound scan using the same 2D ultrasound scan image acquisition parameters and having substantially the same image quality as the 2D ultrasound scan images.

At step 210, the user input module 130 may provide the plane selection module 150 and/or the measurement module 160 with a selected ultrasound image measurement. Additionally and/or alternatively, the measurement may be provided with the 2D ultrasound scan parameters at step 202 or may be associated with a selected examination type, among other things. The selected ultrasound image measurement may be a nuchal translucency measurement, a nuchal fold measurement, a long bone measurement, a fetal head measurement, a vessel measurement, or any suitable measurement.

At step 212, the plane selection module 150 of the signal processor 132 may execute an algorithm to automatically and/or semi-automatically select at least one representative one of the 2D images from the thin slice volume. The thin slice volume includes the last acquired 2D image of the 2D ultrasound scan and the adjacent images acquired during the thin slice volume ultrasound scan. The adjacent 2D images may be in parallel to the last acquired 2D image and/or the thin slice volume may be generated by a volumetric sweep, where the adjacent 2D images are acquired in a fan-like approach. The automatic and/or semi-automatic selection may be based, at last in part, on a selected measurement type, an examination type, or the like. For example, if a user is measuring a fetal head, the plane selection module 150 may select the 2D image from the thin slice volume that is showing the largest diameter. The plane selection module 150 may apply image detection techniques and/or algorithms to automatically and/or semi-automatically select the representative 2D ultrasound image from the thin slice volume. For example, the plane selection module 150 may attempt to identify the representative 2D image automatically. As another example, if a representative 2D image cannot be automatically identified or if the automatically identified image is not satisfactory to a user, the user may select and/or be prompted to select a region or structure in a displayed 2D image to assist the plane selection module 150 in performing a semi-automatic search of the thin slice volume 2D images based on the region and/or structured selected using the user input module 130. Additionally and/or alternatively, the plane selection module 150 may prompt a user for assistance at the onset prior to identifying at least one representative plane in the thin slice volume. In certain embodiments, the plane selection module 150 may define and generate a 2D image slice that is angled across two or more adjacent slices. The at least one representative plane may be displayed at the display system 134 and written to the archive 138.

At step 214, the measurement module 160 may perform the selected measurement on the 2D image selected at step 212. For example, the measurement module 160 may apply a nuchal translucency measurement, a nuchal fold measurement, a long bone measurement, a fetal head measurement, a vessel measurement, or any suitable measurement. The measurement module 160 may display the results of the measurement at the display system 134. The results of the measurement may be overlaid on the measured image or separately, among other things. The measurement may be stored with the measured image in the archive 138, which may be a local archive or PACS, for example.

At step 216, the signal processor 132 may store selected images from the 2D ultrasound scan and/or the thin slice volume ultrasound scan in an archive 138, which may be a local archive or PACS, among other things. In various embodiments, the user input module 130 may be operable to receive a selection identifying one more ultrasound images to store in an archive 138. For example, a user may activate a button 130 on the ultrasound probe 104 to accept and store one or more frames from the 2D ultrasound scan and/or the thin slice volume scan. The accepted and stored ultrasound images may include, for example, a 2D image in a plane of the thin slice volume ultrasound scan that is identified automatically and/or semi-automatically by the plane selection module 150 of the signal processor 132 at step 212. In certain embodiments, the storage of images may be performed automatically by the signal processor 132 based on a default or predetermined setting. For example, the default or predetermined setting may direct the signal processor 132 to automatically store one or more frames from the 2D ultrasound scan, one or more planes from the thin slice volume scan, the representative 2D image identified in step 212, and/or any suitable image or set of images.

At step 218, the examination analysis module 170 of the signal processor 132 may be used to perform post-processing on the acquired or stored images. For example, the examination analysis module 170 may be operable to provide tools for post-processing and otherwise manipulating and storing 2D images and/or thin slice volumes that are displayed at the display system 134. The examination analysis module 170 may be operable to perform 3D rendering on the thin slice volumes and/or to manipulate the thin slice volumes to select a plane based on a user input received at the user input module 130. As an example, after acquiring a thin slice volume or retrieving a thin slice volume from an archive 138, a user can manually identify an image plane by shifting through adjacent planes to set 3 staple points in the thin slice volume and/or may use Z, Y, and Z rotation to set the 3 staple points as described above.

Aspects of the present invention provide a method 200 and system 100 for providing acquisition, enhanced visualization, and selection of at least one representative plane of a thin slice ultrasound image volume. In accordance with various embodiments of the invention, the method 200 comprises performing 204, by an ultrasound probe 104 of an ultrasound system 100, a two-dimensional (2D) ultrasound scan to acquire a plurality of 2D images based on 2D ultrasound scan parameters. The method 200 comprises stopping 208 the 2D ultrasound scan in response to an instruction received by a processor 132 of the ultrasound system 100. The method 200 comprises performing 208, by the ultrasound probe 104 and in response to the instruction, a thin slice volume ultrasound scan to acquire a thin slice volume. The thin slice volume comprises a last acquired 2D image of the 2D ultrasound scan and one or more 2D images adjacent to the last acquired 2D image. The method 200 comprises identifying 212, by the processor 132, 150, at least one representative plane from the thin slice volume. The method 200 comprises displaying 208, by a display system 134 of the ultrasound system 100, the identified representative plane.

In a representative embodiment, the thin slice volume ultrasound scan is performed based on the 2D ultrasound scan parameters. In various embodiments, the thin slice volume ultrasound scan is performed substantially instantaneously after the 2D ultrasound scan is stopped. In certain embodiments, the instruction is provided by a freeze button 130 on the ultrasound probe 104. In a representative embodiment, a thickness of the thin slice volume is based at least in part on a length of time the freeze button 130 is held. In various embodiments, a thickness of the thin slice volume is one of a predetermined value and a default value. The thickness of the thin slice volume is a value in a range of 1 millimeter to 10 millimeters. In certain embodiments, the identified at least one representative plane is one 2D image from the last acquired 2D image of the 2D ultrasound scan and the one or more 2D images adjacent to the last acquired 2D image.

In certain embodiments, the identified at least one representative plane is a plane across multiple 2D images from the last acquired 2D image of the 2D ultrasound scan and the one or more 2D images adjacent to the last acquired 2D image. In a representative embodiment, the method 200 comprises selecting 210 an ultrasound measurement. The at least one representative plane from the thin slice volume is identified 212 based on the selected measurement. In various embodiments, the method 200 comprises performing 218, by the processor 132, 170, three-dimensional (3D) rendering on the thin slice volume. In certain embodiments, the at least one representative plane from the thin slice volume is automatically identified by the processor 132, 150. In a representative embodiment, the at least one representative plane from the thin slice volume is semi-automatically identified by the processor 132, 150. The semi-automatic identification comprises receiving a user input identifying one or more of structure and a location in the thin slice volume. The semi-automatic identification comprises automatically identifying the at least one representative plane from the thin slice volume based at least in part on the user input.

Various embodiments provide a system comprising an ultrasound device 100 that includes an ultrasound probe 104, a processor 132, and a display system 134. The ultrasound probe 104 is operable to perform a two-dimensional (2D) ultrasound scan to acquire a plurality of 2D images based on 2D ultrasound scan parameters. The ultrasound probe 104 is operable to perform a thin slice volume ultrasound scan to acquire a thin slice volume. The thin slice volume comprises a last acquired 2D image of the 2D ultrasound scan and one or more 2D images adjacent to the last acquired 2D image. The processor 132 may be operable to stop the 2D ultrasound scan in response to a received instruction. The processor 132, 140 may be operable to begin the thin slice volume ultrasound scan in response to the received instruction. The processor 132, 150 may be operable to identify at least one representative plane from the thin slice volume. The display system 134 may be operable to display the identified representative plane.

In a representative embodiment, the ultrasound probe 104 comprises a freeze button 130 operable to provide the received instruction. A thickness of the thin slice volume may be based at least in part on a length of time the freeze button 130 is held. In various embodiments, the processor 132, 140 is operable to begin the thin slice volume ultrasound scan substantially instantaneously after stopping the 2D ultrasound scan. In certain embodiments, the thin slice volume ultrasound scan is performed based on the 2D ultrasound scan parameters.

In various embodiments, the processor 132, 150 is operable to identify the at least one representative plane from the thin slice volume one or more of automatically and semi-automatically. The semi-automatic identification comprises the processor 132, 150 operable to receive a user input identifying one or more of structure and a location in the thin slice volume. The semi-automatic identification comprises the processor 132, 150 operable to automatically identify the at least one representative plane from the thin slice volume based at least in part on the user input. In certain embodiments, the system comprises a user input module 130. The user input module 130 is operable to select an ultrasound measurement. The processor 132, 150 is operable to identify the at least one representative plane from the thin slice volume based at least in part on the selected measurement. In a representative embodiment, the processor 132, 170 is operable to perform 3D rendering on the thin slice volume.

Certain embodiments provide a non-transitory computer readable medium having a stored thereon, a computer program having at least one code section that is executable by a machine for causing the machine to perform steps 200 disclosed herein. Exemplary steps 200 may comprise performing 204 a two-dimensional (2D) ultrasound scan to acquire a plurality of 2D images based on 2D ultrasound scan parameters. The steps 200 may comprise stopping 208 the 2D ultrasound scan in response to an instruction received by a processor 132 of the ultrasound system 100. The steps 200 may comprise performing 208, in response to the instruction, a thin slice volume ultrasound scan to acquire a thin slice volume. The thin slice volume comprises a last acquired 2D image of the 2D ultrasound scan and one or more 2D images adjacent to the last acquired 2D image. The steps 200 comprise identifying 212 at least one representative plane from the thin slice volume. The steps 200 comprise displaying 212 the identified at least one representative plane at a display system 134.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the invention may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing acquisition, enhanced visualization, and selection of at least one representative plane of a thin slice ultrasound image volume.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method, comprising: performing, by an ultrasound probe of an ultrasound system, a two-dimensional (2D) ultrasound scan to acquire a real-time video clip with a plurality of 2D images using 2D ultrasound scan parameters; stopping the 2D ultrasound scan in response to an instruction received by a processor of the ultrasound system; performing, by the ultrasound probe and in response to the instruction, a thin slice volume ultrasound scan to acquire a thin slice volume, wherein the thin slice volume comprises a last acquired 2D image of the 2D ultrasound scan and one or more 2D images adjacent to the last acquired 2D image;
identifying, by the processor, at least one representative plane from the thin slice volume; and
displaying, by a display system of the ultrasound system, the identified representative plane.

2. The method according to claim 1, wherein the thin slice volume ultrasound scan is performed based on the 2D ultrasound scan parameters.

3. The method according to claim 1, wherein the thin slice volume ultrasound scan is performed substantially instantaneously after the 2D ultrasound scan is stopped.

4. The method according to claim 1, wherein the instruction is provided by a freeze button on the ultrasound probe.

5. The method according to claim 4, wherein a thickness of the thin slice volume is based at least in part on a length of time the freeze button is held.

6. The method according to claim 1, wherein a thickness of the thin slice volume is one of a predetermined value and a default value, and wherein the thickness of the thin slice volume is a value in a range of 1 millimeter to 10 millimeters.

7. The method according to claim 1, wherein the identified at least one representative plane is one 2D image from the last acquired 2D image of the 2D ultrasound scan and the one or more 2D images adjacent to the last acquired 2D image.

8. The method according to claim 1, wherein the identified at least one representative plane is a plane across multiple 2D images from the last acquired 2D image of the 2D ultrasound scan and the one or more 2D images adjacent to the last acquired 2D image.

9. The method according to claim 1, comprising selecting an ultrasound measurement, wherein the at least one representative plane from the thin slice volume is identified based on the selected measurement.

10. The method according to claim 1, comprising performing, by the processor, three-dimensional (3D) rendering on the thin slice volume.

11. The method according to claim 1, wherein the at least one representative plane from the thin slice volume is automatically identified by the processor.

12. The method according to claim 1, wherein the at least one representative plane from the thin slice volume is semi-automatically identified by the processor, wherein the semi-automatic identification comprises: receiving a user input identifying one or more of structure and a location in the thin slice volume, and automatically identifying the at least one representative plane from the thin slice volume based at least in part on the user input.

13. A system, comprising: an ultrasound device comprising: an ultrasound probe operable to: perform a two-dimensional (2D) ultrasound scan to acquire a real-time video clip with a plurality of 2D images using 2D ultrasound scan parameters, and perform a thin slice volume ultrasound scan to acquire a thin slice volume, wherein the thin slice volume comprises a last acquired 2D image of the 2D ultrasound scan and one or more 2D images adjacent to the last acquired 2D image; a processor operable to: stop the 2D ultrasound scan in response to a received instruction, begin the thin slice volume ultrasound scan in response to the received instruction, and identify at least one representative plane from the thin slice volume; and a display system operable to display the identified representative plane.

14. The system according to claim 13, wherein the ultrasound probe comprises a freeze button operable to provide the received instruction, and wherein a thickness of the thin slice volume is based at least in part on a length of time the freeze button is held.

15. The system according to claim 13, wherein the processor is operable to begin the thin slice volume ultrasound scan substantially instantaneously after stopping the 2D ultrasound scan.

16. The system according to claim 13, wherein the thin slice volume ultrasound scan is performed based on the 2D ultrasound scan parameters.

17. The system according to claim 13, wherein the processor is operable to identify the at least one representative plane from the thin slice volume one or more of:
automatically, and semi-automatically, wherein the semi-automatic identification comprises: the processor operable to receive a user input identifying one or more of structure and a location in the thin slice volume, and the processor operable to automatically identify the at least one representative plane from the thin slice volume based at least in part on the user input.

18. The system according to claim 13, comprising a user input module, wherein the user input module is operable to select an ultrasound measurement, and wherein the processor is operable to identify the at least one representative plane from the thin slice volume based at least in part on the selected measurement.

19. The system according to claim 13, wherein the processor is operable to perform 3D rendering on the thin slice volume.

20. A non-transitory computer readable medium having stored thereon, a computer program having at least one code section, the at least one code section being executable by a machine for causing the machine to perform steps comprising:
performing a two-dimensional (2D) ultrasound scan to acquire a real-time video clip with a plurality of 2D images using 2D ultrasound scan parameters; stopping the 2D ultrasound scan in response to an instruction received by a processor of the ultrasound system; performing, in response to the instruction, a thin slice volume ultrasound scan to acquire a thin slice volume, wherein the thin slice volume comprises a last acquired 2D image of the 2D ultrasound scan and one or more 2D images adjacent to the last acquired 2D image; identifying at least one representative plane from the thin slice volume; and displaying the identified at least one representative plane at a display system.

* * * * *